US011978551B2

(12) United States Patent
Krueger et al.

(10) Patent No.: US 11,978,551 B2
(45) Date of Patent: May 7, 2024

(54) CAMERA ASSISTED SUBJECT SUPPORT CONFIGURATION

(71) Applicant: KONINKLIJKE PHILIPS N.V., Eindhoven (NL)

(72) Inventors: Sascha Krueger, Hamburg (DE); Peter Caesar Mazurkewitz, Hamburg (DE); Julien Thomas Senegas, Hamburg (DE); Steffen Weiss, Hamburg (DE); Jukku Iimari Tanttu, Espoo (FI)

(73) Assignee: Koninklijke Philips N.V., Eindhoven (NL)

( * ) Notice: Subject to any disclaimer, the term of this patent is extended or adjusted under 35 U.S.C. 154(b) by 373 days.

(21) Appl. No.: 17/432,923

(22) PCT Filed: Feb. 24, 2020

(86) PCT No.: PCT/EP2020/054726
§ 371 (c)(1),
(2) Date: Aug. 21, 2021

(87) PCT Pub. No.: WO2020/173849
PCT Pub. Date: Sep. 3, 2020

(65) Prior Publication Data
US 2022/0189622 A1    Jun. 16, 2022

(30) Foreign Application Priority Data

Feb. 25, 2019 (EP) ..................... 19159035

(51) Int. Cl.
*G16H 40/63* (2018.01)
*G06T 7/73* (2017.01)
*G16H 30/20* (2018.01)

(52) U.S. Cl.
CPC ............... *G16H 40/63* (2018.01); *G06T 7/75* (2017.01); *G16H 30/20* (2018.01);
(Continued)

(58) Field of Classification Search
CPC ........ G16H 40/63; G16H 40/67; G16H 50/20; G16H 30/20; G16H 40/20; G16H 50/30;
(Continued)

(56) References Cited

U.S. PATENT DOCUMENTS 5,446,548 A     8/1995   Gerig et al.
5,820,553 A    10/1998   Hughes
(Continued)

FOREIGN PATENT DOCUMENTS

JP    2007267773 A2    10/2007
WO    2016181156 A1    11/2016

OTHER PUBLICATIONS

Dirk Verellen et al."Quality Assurance of a System for Improved Target Localization and Patient Set-Up That Combines Real-Time Infrared Tracking and Stereoscopic X-Ray Imaging" Radiotherapy and Oncology vol. 67, No. Apr. 1, 2003 p. 129-141.
(Continued)

*Primary Examiner* — Ajibola A Akinyemi

(57) ABSTRACT

The invention provides for a medical instrument (100, 300) comprising: a subject support (110) comprising a support surface (112); a camera system (118); and a signal system (148). The execution of the machine executable instructions (152) cause a processor (142) controlling the medical instrument to: receive (400) a list of selected objects (160) each with a selected coordinate (162); and signal (402) the list of selected objects. The Execution of the machine executable instructions further causes the processor to repeatedly: acquire (404) the camera data using the camera system; input (406) the camera data into a neural network to generate a list of placed objects (166); determine (408) a list of missing objects (168) by comparing the list of selected objects to the list of placed objects; indicate (410) using the signal system the list of missing objects; determine (412) a list of misplaced objects (170) by comparing the selected
(Continued)

coordinate for each of the list of objects to the coordinates of the placed objects on the support surface; and indicate (414) using the signal system the list of misplaced objects.

15 Claims, 7 Drawing Sheets

(52) U.S. Cl.
CPC ............ *G06T 2207/10081* (2013.01); *G06T 2207/10088* (2013.01); *G06T 2207/10104* (2013.01); *G06T 2207/10108* (2013.01); *G06T 2207/20084* (2013.01)

(58) Field of Classification Search
CPC ........ G16H 30/40; G16H 40/60; G16H 80/00; G06T 7/70; G06T 2207/10081; G06T 2207/10088; G06T 2207/20081; G06T 2207/30004; G06T 2207/10121; G06T 2207/30204; G06T 7/292; G06T 7/80; G06T 7/97; G06T 2207/10104; G06T 2207/10108
USPC ...................................................... 382/128
See application file for complete search history.

(56) References Cited

U.S. PATENT DOCUMENTS

| | | |
|---|---|---|
| 5,884,350 A | 3/1999 | Kurze |
| 8,080,996 B2 | 12/2011 | Kasugai |
| 9,538,158 B1 | 1/2017 | Rush et al. |
| 10,064,711 B1 | 9/2018 | Richter et al. |
| 11,229,376 B2 | 1/2022 | Pusa et al. |
| 11,256,963 B2 | 2/2022 | Katayama et al. |
| 2003/0225325 A1 | 12/2003 | Kagermeier et al. |
| 2004/0199072 A1 | 10/2004 | Sprouse et al. |
| 2005/0251914 A1 | 11/2005 | Schaller et al. |
| 2009/0182221 A1 | 7/2009 | Kasugai |
| 2012/0100517 A1* | 4/2012 | Bowditch .............. G09B 23/30 434/267 |
| 2013/0113929 A1 | 5/2013 | Deland |
| 2013/0245389 A1 | 9/2013 | Schultz et al. |
| 2016/0331117 A1 | 11/2016 | Follows et al. |
| 2017/0310925 A1* | 10/2017 | Chiang ................. F25D 29/00 |
| 2018/0068179 A1 | 3/2018 | Derenne et al. |
| 2018/0116613 A1 | 5/2018 | Van Berg et al. |
| 2019/0282324 A1* | 9/2019 | Freeman ................. A61B 1/05 |

OTHER PUBLICATIONS

Paolanti Marina "Mobile Robot for Retail Surveying an Inventory Using Visual and Textual Analysis of Monocular Pictures Based on Deep Learning" 2017 European Conf. on Mobile Robots Sep. 6, 2017 p. 1-6.

International Search Report and Written Opinion From PCT/EP2020/054726 dated Sep. 3, 2020.

* cited by examiner

CAMERA ASSISTED SUBJECT SUPPORT CONFIGURATION

CROSS REFERENCE TO RELATED APPLICATIONS

This application is a U.S. national phase application of International Application No. PCT/EP2020/054726 filed on Sep. 24, 2020, which claims the benefit of EP Application Serial No. 19159035.5 filed on Feb. 25, 2019 and is incorporated herein by reference.

FIELD OF THE INVENTION

The invention relates to medical imaging and radiotherapy, in particular to the configuration of a subject support.

BACKGROUND OF THE INVENTION

In both medical imaging and radiotherapy, the physical configuration of the subject being measured as well as various appliances and supports is an important part of configuring an imaging or radiotherapy protocol. For example, in various medical imaging modalities such as magnetic resonance imaging, computed tomography, or positron emission tomography the physical configuration of the subject being measured as well as various appliances and supports are configured differently depending upon the type of examination to be performed. For example, in magnetic resonance imaging depending upon the portion of the subject to be imaged, different types of receive coils may be configured around the subject as well as specialized cushions and supports to position the subject. It can be challenging for an operator of a magnetic resonance imaging system, or other medical imaging system, to correctly and consistently configure it.

United States patent application publication US2009/0182221 discloses a magnetic resonance imaging apparatus that receives magnetic resonance signals emitted from a subject by using a reception coil and reconstructs an image of the test subject from the received magnetic resonance signals, first and second cameras image positions of the subject and the reception coil and an audio recorder records the same to be stored in a PACS server when setting the reception coil. Further, when setting the reception coil for a subsequent time, information of the positions of the test subject and the reception coil is read from the PACS server and confirmed by using a monitor and a speaker.

The US patent application US2018/0116613 mentions the determination of relative positioning of the subject to be imaged and the imaging system (viz. the x-ray source and x-ray detector).

SUMMARY OF THE INVENTION

The invention provides for a medical instrument, a computer program product, and a method in the independent claims. Embodiments are given in the dependent claims.

Embodiments of the invention may reduce the burden of correctly configuring a medical instrument. This is accomplished by imaging a support surface of a subject support with a camera system. As objects or subjects are placed on the support surface, they are imaged by a camera system. These objects add to the configuration of the medical instrument. The camera data from the camera system is input into a neural network that has been trained or configured to output a list of placed objects and coordinates of the placed objects. A list of selected objects each with a selected coordinate can then be compared to the list of placed objects. The list of selected objects can be used to make a list of objects that should be placed on the subject support, whereas the list of placed objects can be used to update which objects have been placed on the subject support and which objects are in the correct position. The comparison of the list of the placed objects and their coordinates with prescribed positioning of the selected objects yields feedback to correct positioning. This feedback may include indications how to displace a misplaced object from its current position to reach its correct position. This correction may be done manually by the operator under guidance from the medical instrument, or the correction may be automatic in that on the basis of the fed back position information, the incorrectly positioned objects are driven to their correct position by the medical instrument.

The invention provides for a medical instrument that comprises a subject support comprising a support surface configured for receiving a subject. The medical instrument further comprises a camera system configured for acquiring image data descriptive of the support surface. The camera system could for example be a two-dimensional camera, a three-dimensional camera, an infra-red, a thermal camera etc., or combinations of all of these. Because the camera system is configured for acquiring image data descriptive of the support surface, objects such as the subject or other objects that are placed on the support surface may be imaged and present in the image data. The medical instrument further comprises a signal system. A signal system may be any device which provides a signal or information to an operator. For example the signal system may be a display. Examples of a display may for example be a projector, a monitor, a television, a tablet, a touchscreen, or other equipment suitable for displaying an image. The signal system may also provide other visual or audible signals such as warning tones or even recorded or synthesized speech.

The medical instrument further comprises a memory for storing machine-executable instructions and a neural network. The neural network is trained or configured for generating a list of placed objects in response to inputting the camera data. The camera data may be images or image data acquired using one or more cameras. The list of placed objects identifies objects placed on the support surface and the coordinates of objects placed on the support surface. The coordinates of the placed objects may be constructed or provided in different ways in different examples. For example, the neural network may identify the placed objects using bounding boxes. The neural network may also identify the location of the entire or a portion of the support surface. This may also be identified with a bounding box. There may be a relationship which has been trained into the neural network or there may be an external program or algorithm which is used to derive the coordinates in relation to the various bounding boxes. For many radiotherapy applications the coordinates on the subject support are given in an indexed or discrete fashion. Typically, the surface of the subject support would be divided into a number of discrete regions. The bounding boxes that are typically output by neural networks could readily be used to derive or calculate these discrete coordinates.

The medical instrument further comprises a processor for controlling the medical instrument. Execution of the machine-executable instructions causes the processor to receive a list of selected objects. The list of selection objects is selected from the predetermined objects. That is to say the list of selected objects is selected from the predetermined objects which have been used to train the neural network. The list of selected objects comprises a selected coordinate for each of the list of objects. The list of selected objects then in other words comprises objects which are able to be identified by the neural network and have coordinates provided for each one of them which indicate where they should be placed on the subject support. Execution of the machine-executable instructions further cause the processor to signal the list of selected objects and the selected coordinates for each of the list of selected objects using the signal system. This may be useful for the medical professional who is setting up the subject support for performing an imaging or radiotherapy protocol. The signal system provides the objects which the healthcare professional needs to properly prepare as well as where these objects should be place on the subject support. Thus, the healthcare professional is guided by the indication where to place proper objects to correctly position them on the subject support The signal system could provide information using audible tones or speech. The signal system could also be a conventional display that outputs or displays information to the subject. In some cases the signal system could provide information by projecting data or positions onto the support surface using a projector or laser.

Execution of the machine-executable instructions further causes the processor to repeatedly acquire the camera data using the camera system. In this step images of the support surface are repeatedly acquired. Next execution of the machine-executable instructions further causes the processor to repeatedly input the camera data into the neural network to generate the list of placed objects. The list of placed objects indicates what objects have been found in the camera data as well as their coordinates.

Execution of the machine-executable instructions further causes the processor to repeatedly determine a list of missing objects by comparing the list of selected objects to the list of placed objects. Objects which have not been placed on the subject support may then be indicated on the list of missing objects. Execution of the machine-executable instructions further causes the processor to repeatedly indicate using the signal system the list of missing objects. This could for example be performed in different ways. It was mentioned earlier that the list of selected objects and their coordinates are signaled using the signal system. The list of missing objects could for example be a separate list of objects or it could be indicated by marking a status or highlighting the list of selected objects in some way. The list of missing objects and/or the list of misplaced objects could also be signaled using audible speech or tones. In other examples the list of missing objects and/or the list of misplaced objects is signaled by projecting graphical images or locations onto the subject surface using a projector or a laser. This guides the operator to add missing objects at their proper positions.

Execution of the machine-executable instructions further causes the processor to determine a list of misplaced objects by comparing the selected coordinate for each of the list of objects to the coordinates of the placed objects on the support surface. Execution of the machine-executable instructions further causes the processor to indicate using the signal system the list of misplaced objects. Again, the indication of the list of misplaced objects could be performed in different ways. For example, there may be a separate list of objects which are in the wrong location or the display of the list of selected objects may be modified so that it is apparent that the coordinates of where a particular object is not where it was specified in the list of selected objects and the selected coordinate for each of those.

This embodiment may be beneficial because it may provide an automated means of providing a list of what objects should be placed onto the subject support and in what locations. Not only is the list of selected objects in the selected coordinate signaled but also the neural network is used to check to make sure that the proper items or objects are placed on the support surface as well as in the proper location. This adds to automation of guiding the user in placing the proper items in their correct positions.

The training of the neural network may be performed using images of different objects placed on the subject support. Deep training could be used to train both the coordinate and the identity of a particular object. This adds to providing three-dimensional guidance to the user in setting up the configuration of objects.

An object of the present invention is to provide guidance on correctly technically configuring the medical instrument for carrying-out a particular imaging protocol. To that end a neural network is provided which generates a list of placed objects from camera data (images of the configuration) and identifies objects placed on the support surface (e.g. using bounding boxes). These objects add to the configuration of the medical instrument, e.g. to support the subject that is to undergo an action of the medical instrument. Such actions may be diagnostic imaging or a therapeutic action. Thus, the objects add to the configuration that supports or even enables the action of the medical instrument to the subject. The neural network recognises placed objects from the images from the camera. The neural network is trained for the recognition of predetermined objects. Further, a list of selected objects is received that is associated with the imaging protocol to be carried-out. These selected objects and their coordinates are then signaled to the user in order to have them placed at their respective proper positions. That is, the invention indicates which objects need to be prepared and where they are to be placed on the subject support. This may be done in a sequential order to allow monitoring of objects that may be placed on top of each other, or may be partially obscured from the view of the camera as the configuration is being built-up. In this way the healthcare professional is guided in properly configuring the medical instrument for the relevant medical (e.g. imaging or treatment) protocols. Also recording may be done of the actually used objects how they were configured for performing the protocol. The invention may automatically log missing or misplaced objects. A list of missing and/or misplaced objects may be provided to the medical system's user interface. Notably, the invention adds to better reproducibility of the configuration e.g. for imaging for therapy planning and for actual delivery of therapy, notably in radiation therapy.

The medical instrument of the invention provides information on the actual configuration of objects on the subject support including presence or absence of objects and whether they are in the correct position. This feedback also provides information on which objects are to be added or replaced, at which position and also how an actual position of a misplaced object relates to its proper correct position. That is, the medical instrument of the invention provides for technical guidance to the user to build-up an appropriate configuration of the medical instrument to be applied to a subject (i.e. patient to be examined or patient to be treated). In an embodiment of the medical instrument, the subject support may be automatically moved from its initial position to its operating position. In its initial position, the configuration of objects may be built-up under guidance from the camera system and the subject be accurately positioned. In the operational position of the subject support, the configuration of objects with the subject is in position for the subject to undergo medical instrument's operation according to the protocol.

The neural network determines which objects are present and in their correct positions. Further the neural network is operative to generate feedback in the form of a list of placed objects, missing objects and misplaced objects. The use of the neural network provides technical guidance to the user for accurate setting up the correct configuration for the protocol to be executed. The feedback repeatedly provides feedback on the configuration as it is built-up, if and how it deviates from the correct configuration and how corrections are to be made. The neural network provides technical guidance in setting up the technical configuration in an accurate and efficient manner for the relevant protocol. The information generated on the correctly placed, missing or misplaced objects constitutes actual information on the internal technical state of the medical instrument as the configuration is being built up and on the correct configuration being reached. The neural network also provides information on which objects are still to be positioned and how to re-position misplaced objects so that they reach their proper positions.

In another embodiment execution of the machine-executable instructions further causes the processor to signal the list of selected objects in a sequential order defined in the list of selected objects using the signal system. This may be beneficial because in configuring the objects on the subject support it may be beneficial to put them on the subject support in a particular order. This may be useful for example when one object needs to be placed above or over another object or when one object may be partially obscured by another object. This embodiment may be beneficial because it may assist the healthcare professional in properly configuring the medical instrument.

In another embodiment execution of the machine-executable instructions further causes the processor to determine a list of properly positioned objects using the list of placed objects, the list of missing objects, and the list of misplaced objects. Execution of the machine-executable instructions further causes the processor to generate a signal if a member of the properly positioned objects is identified within misplaced objects and/or the missing objects. In this embodiment if an object that was previously correctly positioned is then moved to an improper location or is removed, then the signal is provided. The signal may take different forms in different examples. For example, the signal may be a visual or audible signal which may alert a healthcare professional that an unauthorized deviation from the standard protocol has occurred. The signal could also prompt a notice or signal from the signal system. In other examples the signal could be used to log the objects that are identified as being on the subject support and their coordinates. This may be useful in recording the objects that were actually used for performing a medical imaging protocol.

In another embodiment, the medical instrument comprises a medical imaging system configured for acquiring medical image data from an imaging zone. The support surface is configured for supporting at least a portion of the subject within the imaging zone.

In another embodiment the memory further comprises an imaging protocol database. The imaging protocol database comprises lists of selected objects each associated with an imaging protocol. Execution of the machine-executable instructions further causes the processor to receive a selection of a medical imaging protocol. Execution of the machine-executable instructions further causes the processor to receive the list of selected objects from the medical imaging protocol database using the selection of the medical imaging protocol. In this embodiment the selection of the medical imaging protocol is an instruction which chooses a particular imaging technique and/or region of the subject. Based on this selection the proper list of selected objects is retrieved from the medical imaging protocol. This for example may be useful in assisting a medical professional in setting up the medical instrument for a large number or diverse number of different medical imaging protocols. That is the medical instrument provides guidance to the user to position the objects in dependence of the selected imaging protocol.

In another embodiment the selected coordinate for each of the list of objects is specified in discrete coordinates. The coordinates of the placed objects on the subject support are specified in the discrete coordinates. A discrete coordinate as used herein is a coordinate system which divides the subject support into discrete regions. When placing an object on the subject support the use of the discrete coordinates specifies within which region or regions the object should be placed. Within these particular regions the healthcare professional then has the freedom to place it wherever as long as it was within the volumes or regions specified by the discrete coordinates. This may be beneficial because such coordinate systems are typically used in setting up objects and structures for radiotherapy.

In another embodiment execution of the machine-executable instructions further causes the processor to append a status of the list of misplaced objects and the list of missing objects to the medical image data. This may be beneficial because it may provide for a means of automatically logging which objects are missing or not placed in the standard position when the medical imaging was performed. For example, the DICOM file could have information about the setup recorded in an automated manner. The status list of misplaced objects and the list of missing objects may be detailed about what is missing or not missing or may just be meta data describing if these lists were empty or not.

In another embodiment execution of the machine-executable instructions further causes the processor to append the list of placed objects and the coordinates of the placed objects to the medical image data. Again, this could be done in for example the DICOM file format and these lists are appended in an automated fashion.

In another embodiment the subject support is configured to move from an initial position to an operating position. In the initial position the camera system is configured for performing the acquiring of the camera data descriptive of the subject support. In the operating position the subject support is configured for supporting at least a portion of the subject within the imaging zone. This for example may be descriptive of many different medical imaging systems such as magnetic resonance imaging or computer tomography where the subject and any supports or supporting objects are first positioned on a subject support and then the subject is injected into a medical imaging system and/or a radiotherapy system.

Execution of the machine-executable instructions further causes the processor to repeatedly provide a user interface control using the signal system after repeatedly signaling using the signal system the list of missing objects and the list of misplaced objects. Execution of the machine-executable instructions further causes the processor to generate an acceptance command if a signal is received from the user interface control. Execution of the machine-executable instructions further causes the processor to move the subject support from the initial position to the operating position if the acceptance command is generated. Execution of the machine-executable instructions further causes the processor to control the medical imaging system to acquire the medical image data when the subject support is in the operating position. This embodiment may be beneficial because the user interface control enables the operator of the medical instrument to commence medical imaging even if the objects in the list of selected objects are not all present and/or not in the position specified in the list of selected objects.

In another embodiment execution of the machine-executable instructions further causes the processor to append the list of placed objects and their coordinates to the medical image data in response to the signal being received from the user interface control. This may be beneficial because it may be useful for automatically recording the objects actually used on the subject support during a medical imaging protocol.

In another embodiment execution of the machine-executable instructions further causes the processor to store the camera data with the medical image data. This may for example be the appending of the camera data to a DICOM file or equivalent. This may be useful in doing automatic archiving of the conditions used when the medical image data was acquired.

In another embodiment the predetermined objects comprise the subject. The neural network is further configured for identifying a subject orientation or position. This may for example be useful because it may provide instructions on how the subject should be positioned on the subject support. These instructions may guide the user to position the subject relative to the already built-up configuration of objects.

In another embodiment the predetermined object comprises any one of the following: a cushion, a head mirror, a headrest, a knee rest, an armrest, a magnetic resonance imaging coil, a footrest, an ankle rest, and combinations thereof.

In another embodiment the medical instrument further comprises a radiotherapy system configured for irradiating a target zone. The target zone is within the imaging zone.

In another embodiment the medical imaging system is configured for guiding the radiotherapy system during irradiation of the target zone. This embodiment may be beneficial because the use of the system for placing the objects on the subject support may enable more repeatable radiotherapy for a subject. This, the guidance by the medical instrument to build-up the configuration of objects enables more accurate reproduction of the positioning between imaging/planning and the actual delivery of therapy In another embodiment the medical imaging system is a magnetic resonance imaging system.

In another embodiment the medical imaging system is a computer tomography system.

In another embodiment the medical imaging system is a positron emission tomography system.

In another embodiment the medical imaging system is a single photon emission tomography system.

In another embodiment the imaging system comprises a video camera.

In another embodiment the imaging system comprises a camera.

In another embodiment the imaging system comprises a color camera.

In another embodiment the imaging system comprises a black and white camera.

In another embodiment the imaging system comprises an infra-red camera.

In another embodiment the imaging system comprises a thermal camera.

In another embodiment the imaging system comprises multiple cameras.

In another embodiment the imaging system comprises a three-dimensional camera.

In another aspect the invention provides for a computer program product comprising machine-executable instructions for execution by a processor controller a medical instrument. The medical instrument further comprises a subject support comprising a support surface configured for receiving a subject. The medical instrument further comprises a camera system configured for acquiring camera data descriptive of the support surface. The medical instrument further comprises a signal system.

Execution of the machine-executable instructions further cause the processor to receive a list of selected objects. The list of selected objects is selected from predetermined objects. The list of selected objects comprises a selected coordinate for each of the listed objects. Execution of the machine-executable instructions further causes the processor to signal the list of selected objects and the selected coordinate for each of the list of selected objects using the signal system.

Execution of the machine-executable instructions further causes the processor to repeatedly acquire the image data using the camera system. Execution of the machine-executable instructions further causes the processor to repeatedly input the camera data into a neural network to generate a list of placed objects. The neural network is trained or configured for generating the list of placed objects in response to inputting the camera data. The list of placed objects identifies predetermined objects placed on the support surface and coordinates of the placed objects on the support surface.

Execution of the machine-executable instructions further causes the processor to repeatedly determine a list of missing objects by comparing a list of selected objects to the list of placed objects. Execution of the machine-executable instructions further causes the processor to further cause the processor to indicate using the signal system the list of missing objects. Execution of the machine-executable instructions further causes the processor to determine the list of misplaced objects by comparing the selected coordinate for each of the list of objects to the coordinates of the placed objects on the support surface. Execution of the machine-executable instructions further causes the processor to repeatedly indicate using the signal system the list of misplaced objects.

In another aspect the invention provides for a method of operating a medical instrument. The medical instrument further comprises a subject support comprising a support surface configured for receiving a subject. The medical instrument further comprises a camera system configured for acquiring image data descriptive of the support surface. The medical instrument further comprises a signal system.

The method comprises receiving a list of selected objects. The method further comprises signaling the list of selected objects and the selected coordinates for each of the list of selected objects using the signal system. The method comprises repeatedly acquiring the camera data using the camera system. The method comprises repeatedly inputting the camera data into a neural network to generate a list of placed objects. A neural network is trained for generating a list of placed objects in response to inputting the image data. The list of placed objects identifies predetermined objects placed on the support surface and coordinates of the placed objects on the support surface. The list of selected objects is selected from the predetermined objects.

The list of the selected objects comprises a selected coordinate for each of the listed objects. The method further comprises determining a list of missing objects by comparing the list of selected objects to the list of placed objects. The method further comprises indicating using the signal system the list of missing objects. The method further comprises determining a list of misplaced objects by comparing the selected coordinate for each of the list of objects to the coordinates of the placed objects on the support surface. The method further comprises repeatedly indicating using the signal system the list of misplaced objects.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two- or three-dimensional data that has been acquired using a medical imaging scanner. A medical imaging system is defined herein as an apparatus adapted for acquiring information about the physical structure of a subject and construct sets of two-dimensional or three-dimensional medical image data. Medical image data can be used to construct visualizations which are useful for diagnosis by a physician. This visualization can be performed using a computer Magnetic Resonance imaging data or magnetic resonance data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
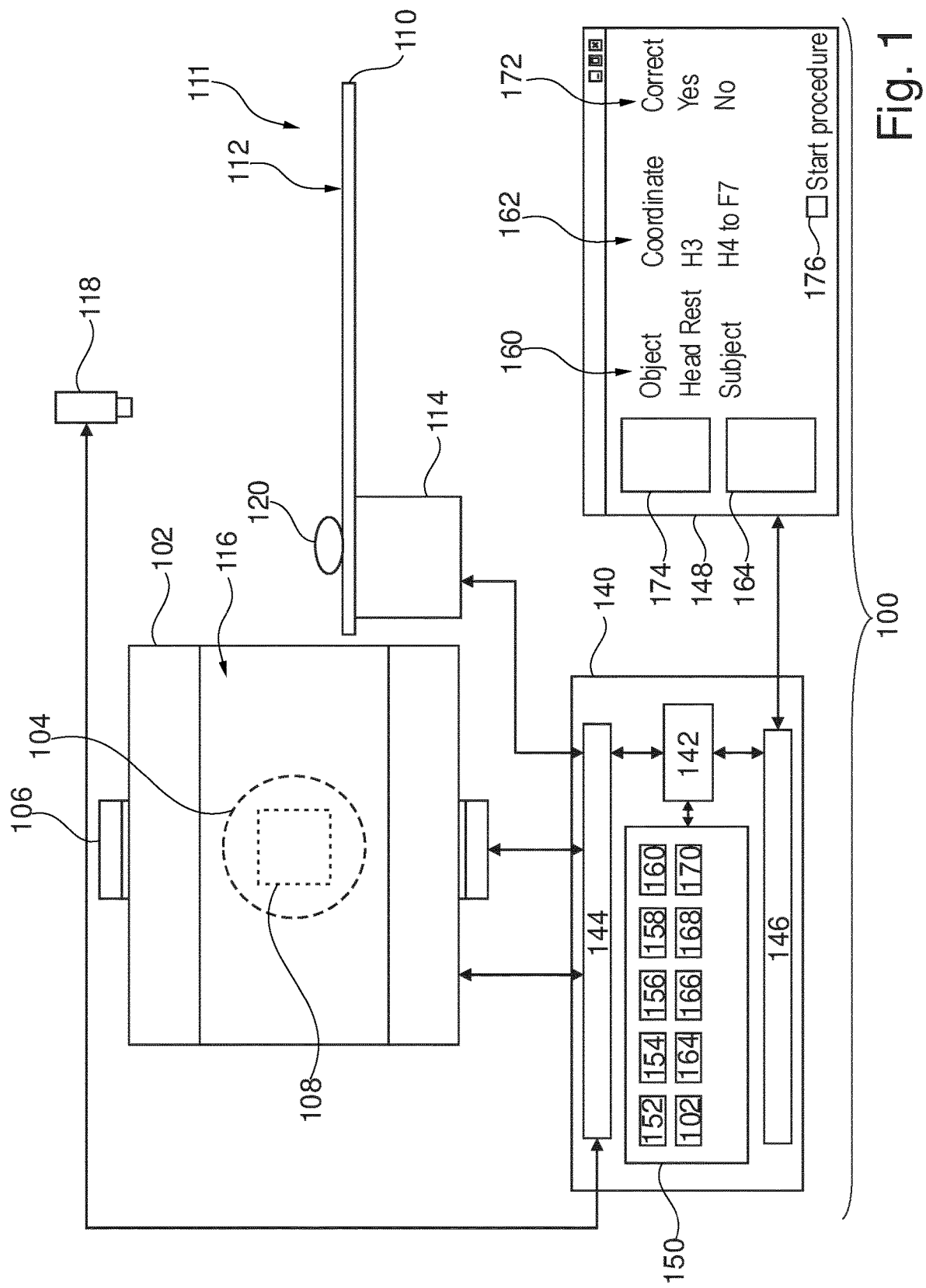
FIG. 1 illustrates an example of a medical instrument.

FIG. 1 illustrates an example of a medical instrument 100. The medical instrument 100 is shown as optionally comprising a medical imaging system 102 that is configured for acquiring medical image data from an imaging zone 104. The medical instrument 100 is also shown as also containing an optional radiotherapy system 106. In this example, optional radiotherapy system 106 is configured for irradiating a target zone 108 that is within the imaging zone 104. If present, the medical imaging system 102 can therefore be used to guide the radiotherapy system 106. In some examples the medical instrument 100 does not comprise either the medical imaging system 102 or the radiotherapy system 106.

Figure 2:
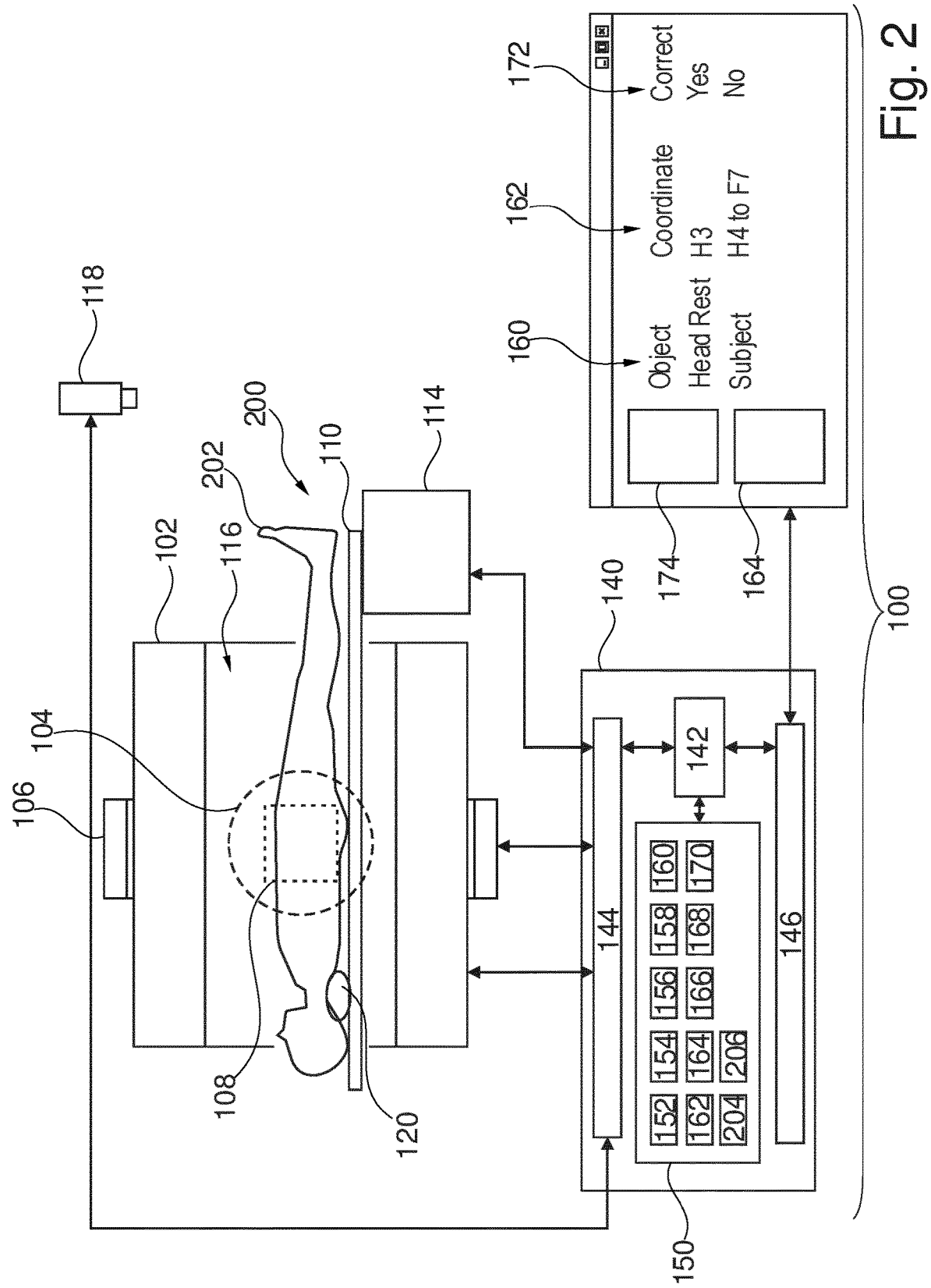
FIG. 2 shows a further view of the medical instrument of FIG. 1.

There is a subject support 110 which is configured for receiving a subject. The subject support 110 is shown in an initial position 111. In the initial position 111 a support surface 112 is able to be imaged by a camera system 118. The camera system 118 may for example be configured for taking still and/or video feeds which show objects 120 on the support surface 112. In this example there is a single headrest 120 that is sitting on the support surface 112. The medical instrument 100 is also shown as comprising an actuator 114 that is configured for moving the subject support 110 from the initial position 112 into an operating position which is illustrated in FIG. 2. The medical imaging system 102 is cylindrical and has a bore 116 into which the subject support 110 can be inserted or injected. Any objects on the surface 112 such as a subject or other object 120 will be moved into the bore 116 also.

The medical instrument 100 is further shown as containing a computer 140. The computer 140 comprises a processor 142 that is connected to a hardware interface 144. The hardware interface 144 enables the processor 142 to control the operation of the other components. The camera system 118, the medical imaging system 102 and the radiotherapy system 106 are all shown as being connected to the hardware interface 144. The processor 142 is further connected to a user interface 146 and a memory 150. The user interface 146 also comprises a signal system 148. In this example the signal system is a display 148.

However, the display 148 could be replaced with a different type of signal system. A computer speech system could be used to indicate the information in the display in an audible fashion. The information shown in the display 148 could also be project graphically onto the support surface 112 using a laser or a projector.

The memory 150 may be any combination of memory which is accessible to the processor 142. This may include such things as main memory, cached memory, and also non-volatile memory such as flash RAM, hard drives, or other storage devices. In some examples the memory 150 may be considered to be a non-transitory computer-readable medium.

The memory 150 is shown as containing machine-executable instructions 152. Execution of the machine-executable instructions 152 enables the processor 142 to perform tasks such as controlling the other components and also doing basic image and mathematical procedures. The memory 150 is further shown as containing a neural network 154. The neural network 154 receives camera data 164 from the camera 118 and outputs a list of placed objects 166. The memory 150 is shown as containing an optional imaging protocol database 156 which contains details of various imaging protocols which can be performed by the medical instrument 100. The processor 142 may for example receive a selection of a medical imaging protocol 158. This may be used to retrieve a list of selected objects 160 from the optional imaging protocol database 156. The list of selected objects 160 also contains selected coordinates 162 which indicate the position of objects 120 that should be placed on the surface 112. The user interface 148 is shown as displaying the list of selected objects 160 and their coordinates 162.

The memory 150 is shown as storing copies of both the list of selected objects 160 and the selected coordinates 162. The memory 150 is further shown as containing camera data 164. The camera data 164 was then input into the neural network 154 and used to generate a list of placed objects 166. The list of placed objects 166 was then compared to the list of selected objects 160 and the selected coordinates 162 to generate a list of missing objects 168 and a list of misplaced objects 170 which are both shown stored in the memory 150. There may be an indicator 172 on the display 148 which indicates if there are any misplaced 170 or missing 168 objects.

The user interface 148 is further shown as containing a rendering of the camera data 164. This may for example be useful to a medical professional who is configuring the medical instrument 100. Optionally, there may be an archive image 174 which shows either a partial or completely configured surface 112. This may for example be an additional guide to assist the healthcare professional. The user interface 148 is also shown as having an optional user interface control 176 which can be used to trigger insertion of the subject support 110 into the bore 116. For example, in some instances the operator may not necessarily want to follow the list of selected objects 160 and the selected coordinates 162 exactly. The use of the optional user interface control 176 gives the operator the option to perform the imaging protocol anyway.

FIG. 2 shows a further view of the medical instrument 100. In this view the actuator 114 was used to move the subject support 110 into the bore 116. The subject support 110 is now in the operating position 200. The subject 202 is shown as being reposing on the subject support 110. A portion of the subject 202 can be imaged in the imaging zone 104 and the radiotherapy system 106 can be used to irradiate locations within the target zone 108. The memory 150 is shown as containing medical image data 204 that was acquired by controlling the medical imaging system 102. The memory 150 is further shown as containing a medical image 206 that was reconstructed from the medical image data 204. The medical image 206 may for example be used for guiding irradiation of the subject 202 by the radiotherapy system 106.

Figure 3:
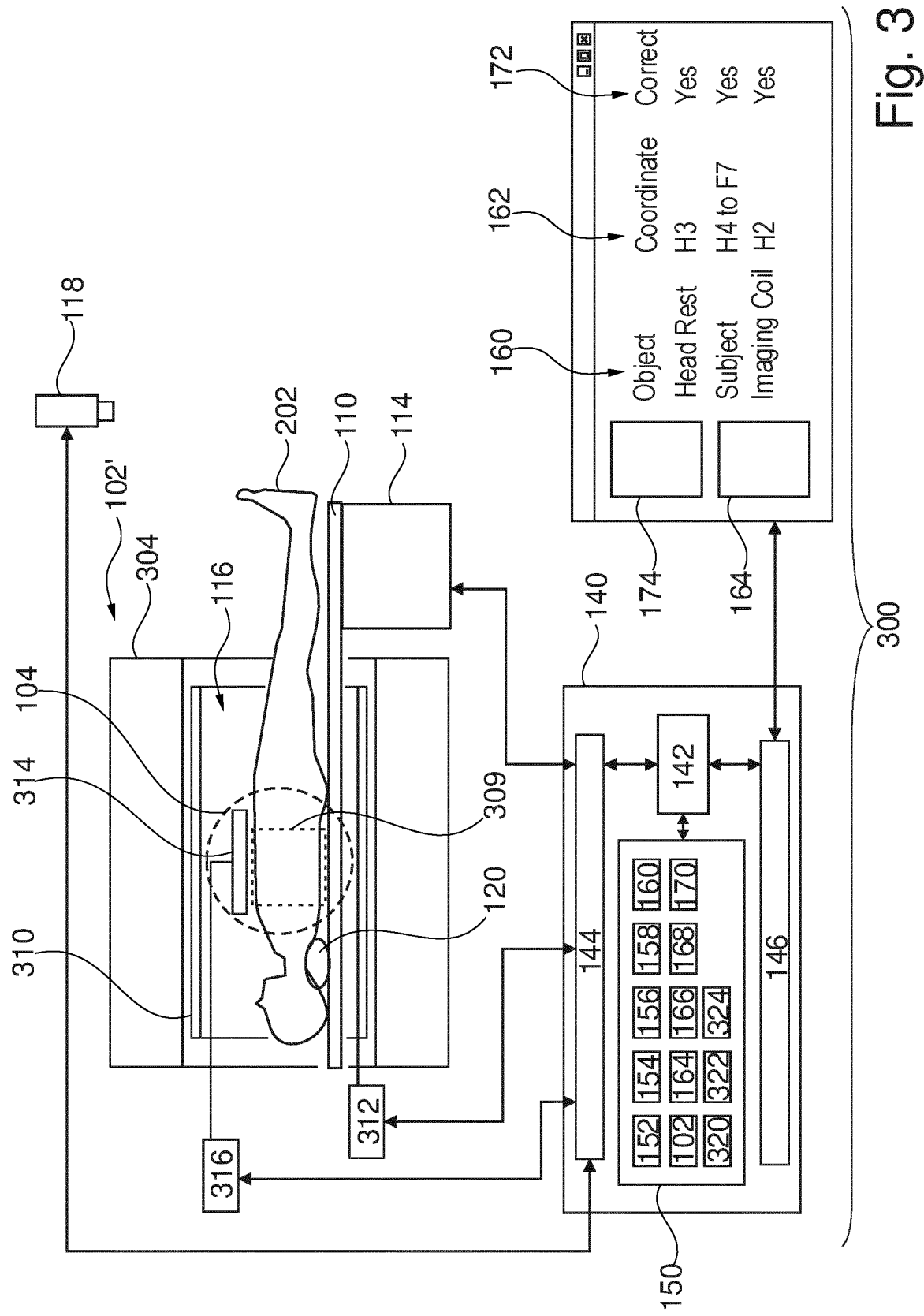
FIG. 3 illustrates a further example of a medical instrument.

FIG. 3 shows a further example of a medical instrument 300. In this example the medical imaging system is a magnetic resonance imaging system 102'. The magnetic resonance imaging system 102' comprises a magnet 304. The magnet 304 is a superconducting cylindrical type magnet with a bore 116 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 116 of the cylindrical magnet 304 there is an imaging zone 108 where the magnetic field is strong and uniform enough to perform magnetic resonance imaging. A region of interest 309 is shown within the imaging zone 104. The magnetic resonance data that is acquired typically acquired for the region of interest. A subject 202 is shown as being supported by a subject support 110 such that at least a portion of the subject 118 is within the imaging zone 104 and the region of interest 309. The subject support is in the operating position 200.

Within the bore 116 of the magnet there is also a set of magnetic field gradient coils 310 which is used for acquisition of preliminary magnetic resonance data to spatially encode magnetic spins within the imaging zone 104 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 104 is a radio-frequency coil 314 for manipulating the orientations of magnetic spins within the imaging zone 104 and for receiving radio transmissions from spins also within the imaging zone 104. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316, the gradient controller 312, and camera system are shown as being connected to the hardware interface 144 of the computer system 140. The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions.

The memory 150 is shown as containing pulse sequence commands 320. The pulse sequence commands are commands or data which may be transformed into commands which are used to control the magnetic resonance imaging system 102' to acquire magnetic resonance imaging data 322. The memory 150 is shown as containing magnetic resonance imaging data 322 that was acquired by controlling the magnetic resonance imaging system with the pulse sequence commands 320. The magnetic resonance imaging data 322 is an example of medical image data. The memory 150 is further shown as containing a magnetic resonance image 324 that was reconstructed from the magnetic resonance imaging data 322.

Figure 4:
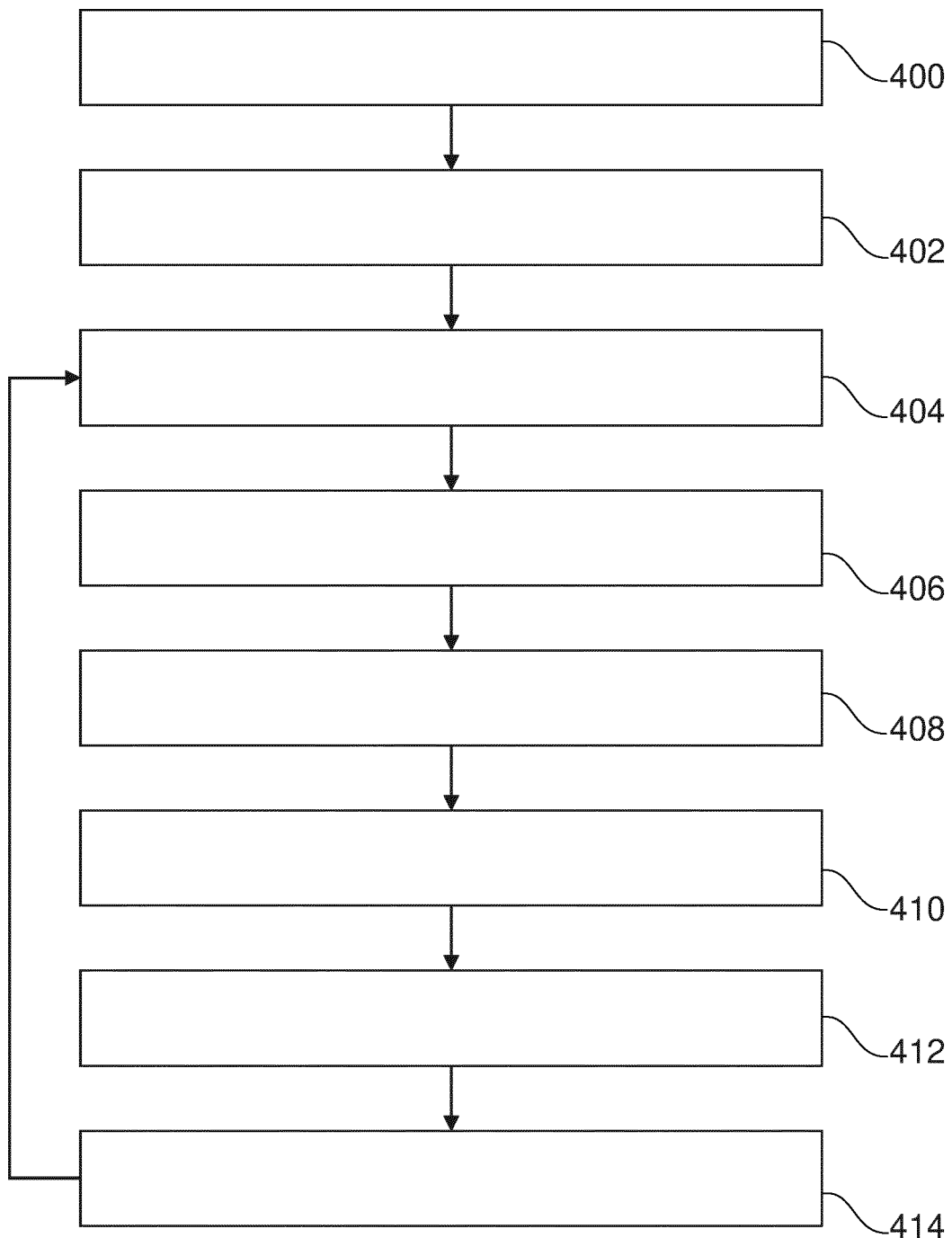
FIG. 4 shows a flow chart which illustrates a method of operating the medical instrument of FIG. 1 or FIG. 3.

FIG. 4 shows a flowchart which illustrates a method of operating either the medical instrument illustrated in FIGS. 1 and 2 or the medical instrument 300 illustrated in FIG. 3. First in step 400 the list of selected objects 160 is received. The list of selected objects is selected from the predetermined objects which were used to train the neural network. The list of selected objects comprises a selected coordinate for each of the listed objects 162. Next in step 402 the list of selected objects 160 and the selected coordinate 162 for each of the selected objects is displayed on the display 148. The method then proceeds to steps 404-414. The method steps 404-414 are performed in a loop. An operator may voluntarily halt this loop or it may for example halt when it is selected or decided to initiate imaging of the subject. In step 404 the camera data 164 is acquired using the camera system 118. Then in step 406 the camera data 164 is input into the neural network 154 to generate the list of placed objects 166. Then in step 408 a list of missing objects 168 is determined by comparing the list of selected objects 160 to the list of placed objects 166. In step 410 the list of missing objects 168 is indicated 172 on the display 148. After step 410 the method proceeds to step 412 where the list of misplaced objects 170 is determined by comparing the selected coordinate for each of the listed objects to the coordinates of the placed objects on the support surface 112. Then in step 414, the list of misplaced objects 168 is indicated 172 on the display 148. Steps 408 and 412 may be interchanged. The method then proceeds from step 414 back to step 404 in a loop.

Figure 5:
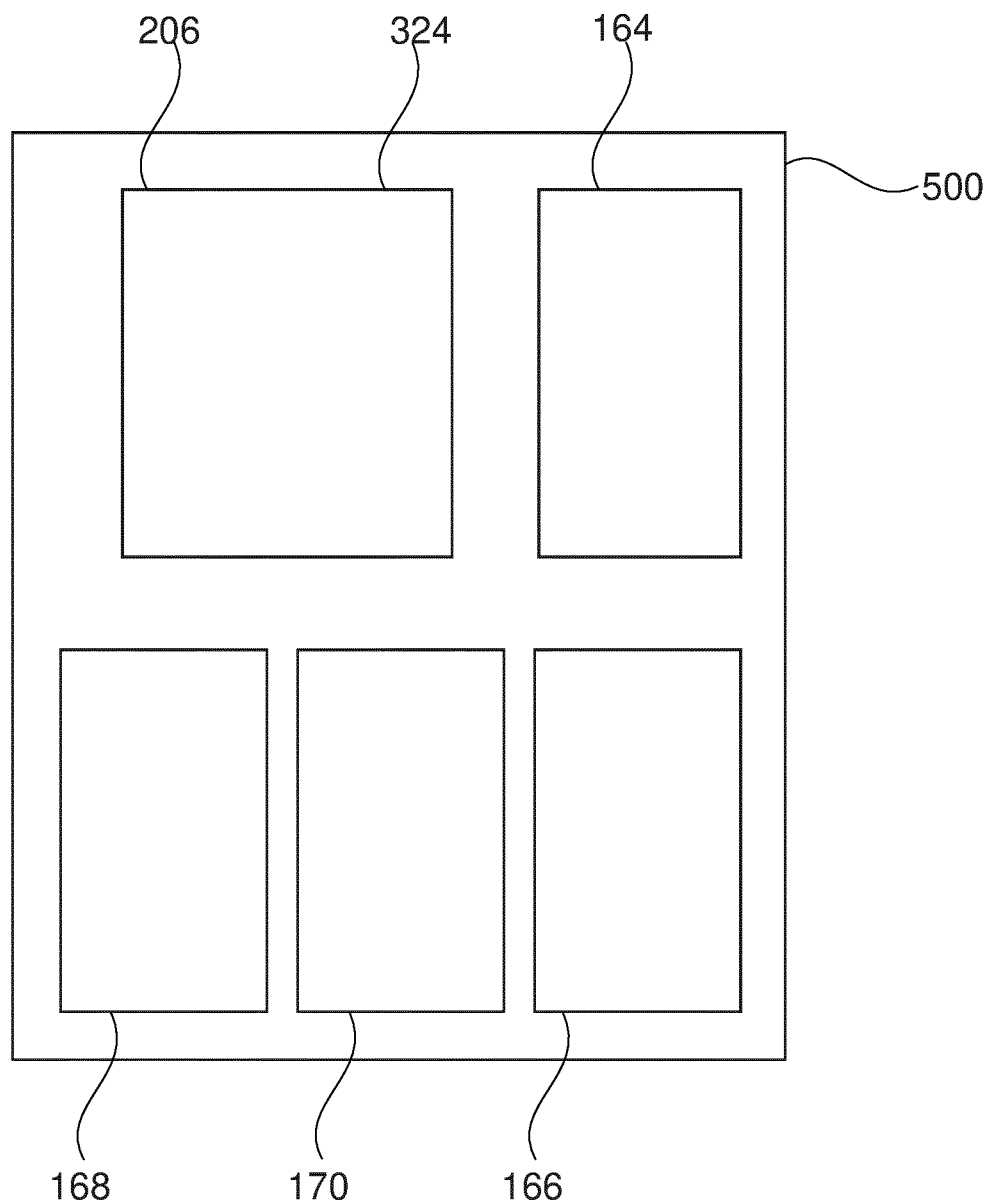
FIG. 5 graphically illustrates the contents of a DICOM file.

FIG. 5 illustrates an example of a medical imaging file 500. The medical imaging file 500 could for example be a container or file which is used to archive or store medical images acquired using the medical instrument 100 shown in FIGS. 1 and 2 or the medical instrument 300 illustrated in FIG. 3. The medical image file 500 could for example be a DICOM file. The medical imaging file 500 may for example include the medical image 206 or the magnetic resonance image 324. The medical image file 500 could also possibly contain the camera data 164 acquired with the camera system 118. This may be useful as an archival record of what was used to configure the medical apparatus 100 or 300. The medical imaging file 500 may also contain the list of placed objects 166. This may be useful as an auto generated list of what was used and the coordinates that were used to place it on the subject support 110. The medical imaging file 500 may also optionally contain the list of missing objects 168 and/or the list of misplace objects 170. The medical imaging file 500 may for example be auto generated when the medical image 206 or the magnetic resonance image 324 is reconstructed.

As was mentioned above, preparing a subject 202 for an examination is a time-consuming task and requires trained skills of the operator. The operator may place positioning devices (e.g. knee support, head rest) to secure a stable resting position of the subject throughout the examination or has to place coils 314 (MRI) and accessories 120, 802 (i.e., sensors) adequately to obtain repeatable image quality. In repeated or follow-up scans, and in scans for treatment planning, monitoring and respective treatment sessions, it may be beneficial to reproduce the previous subject set-up and respective images in same quality to make them comparable. In radiation therapy for example, the exact subject set-up is commonly reproduced as closely as possible for up to 40 radiation delivery sessions. For exact but still fast repositioning of all devices, subject supports in therapy planning are frequently equipped with mechanical means to allow only a finite set of positions. One example is given in FIG. 6 below where the knee support can only be positioned at discrete positions H4 to F7. Quality assurance requires to accurately report all relevant setup information in detail during each session to be able to compare and reproduce the setup. This is a time-consuming and error-prone task.

Figure 6:
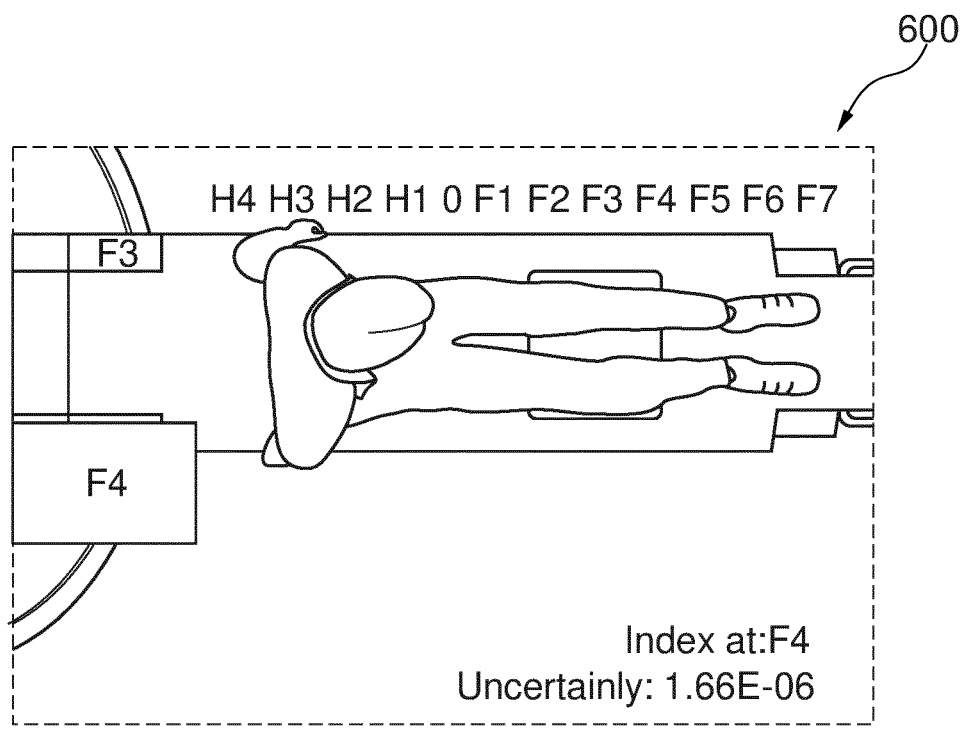
FIG. 6 illustrates the functioning of an example system.
Figure 7:
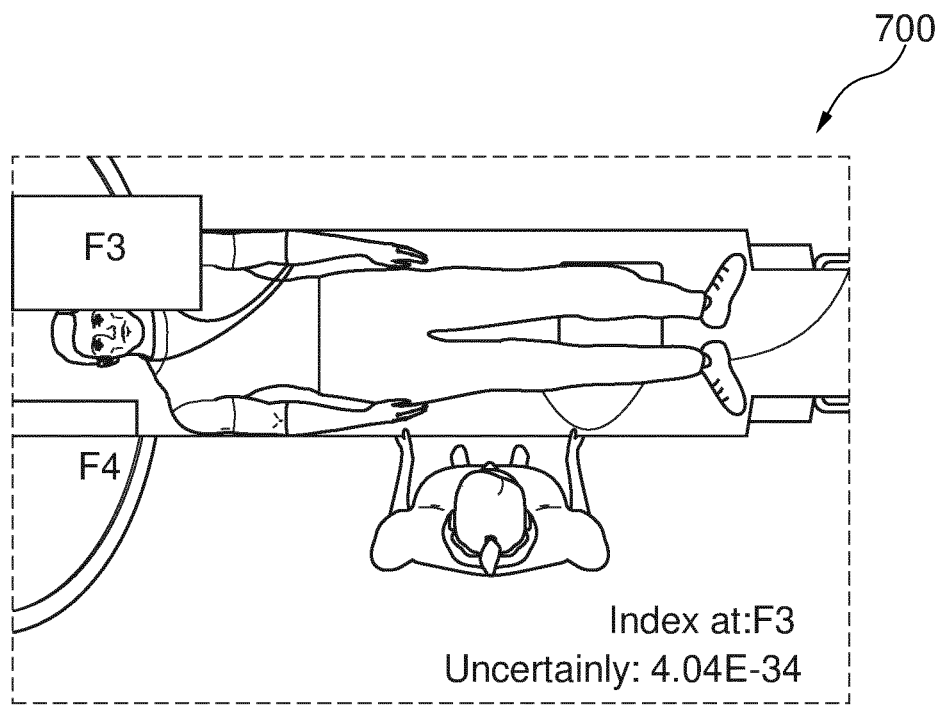
FIG. 7 further illustrates the functioning of the example system of FIG. 6.

FIGS. 6 and 7 illustrate a proof of concept of examples. In FIG. 6 the image 600 shows an automatically detected knee positioning device at the table index location 4 in the feet direction or F4. This was performed using a trained classification neural network or a neural network. In FIG. 7 a correct classification of a small index bar at location F3 in a more complex scene with partial obstructions, table movement and misleading hand gestures was still successful.

For radiotherapy planning, there are RFID based system to check presence of correct types of positioning devices and respective location. The system may use a number of RFID sensors integrated into a set of positioning devices and indexing/holder devices. The system can be used with a set of registered devices which are equipped with such a system. While RFIDs help to automate, reproduce and safeguard the setup reporting and reproduction workflow, the system has limitations in reporting the full complexity of a typical subject setup. Often custom or 3rd-party devices are used which are not known to the system and which cannot be easily equipped with RFIDs. Some devices are not suited for installation along a fixed predefined raster index (e.g. support wedges, padding or cushions, or custom made subject-specific devices). All these devices will not be included into the setup report and will limit the ability to reproduce. Also, RFIDs may fail individually and thus the likeliness of an error increases with the number of devices. More complex subject setups cannot be reproduced with such a system because a step-by-step guidance to achieve the correct result is missing. RFIDs also represent an RF safety issue which leads to increased integration effort and costs. Also, RFID is a short-range communication technique and will fail if the distance gets too far. RFID technology may also be heavily disturbed by RF interference, especially when used with other large electric equipment like medical imaging devices.

Examples may use a camera-based 118 subject 202 setup classification and reproduction system to detect types and locations of used positioning devices. A neural network may be trained to classify an image in one of several classes: each class corresponds to a given target device (e.g. knee positioning device) at a given position (e.g. index position F4). Ideally, one class corresponds to the target device being not present. The system can be more complex to handle classes made of several devices or handle combinations of classes. During subject setup, the trained neural network determines the list of installed devices and their location classes, together with a confidence level for the determined device and location (see FIGS. 6 and 7). A location class that was determined with low confidence indicates improper installation with high sensitivity. This may be used to trigger an alarm (or signal) that reminds the staff to correct positioning. It is proposed to automatically store the raw camera images that were used to classify a scene for quality control as is illustrated in FIG. 5. The camera system works from a distance and does not interfere with the workflow. It can classify type and positioning classes (e.g. an index) of setup components while being sensitive to all spatial directions thus covering a larger setup manifold than would be possible with an RFID system. The proposed approach has several further advantages: No markers or modifications to the devices are needed. Sterility and safety issues of such devices are therefore avoided. Since it works optically it is not prone to RF interference as long as standard means to shield the camera electronics against spurious RF are provided. The term camera or camera system 118 may include cameras that produce an image (camera data): e.g. RGB, monochrome, infrared, thermal and 3D (stereo, time-of-flight, structured light, LADAR, RADAR) cameras.

The use of a camera system 118 allows to use a larger variety of devices from arbitrary vendors at lower cost. Device types and locations can be detected from the images provided by the camera system using neural networks. The system is scalable, i.e. can be extended to more device types or further device location or pose classes. Such a system would allow classification of the setup on a much higher abstraction level. A camera system would also provide clearer failure paths, e.g. if the camera may break this can be easily detected. Or if the classification is erroneous the recorded camera image would be indicative of individual errors and the setup could still be reproduced with high accuracy. The system can be applied to general tomographic imaging and would allow extreme reproducibility on follow up examinations removing the necessity of complex changes is the scan protocols while providing persistent level of image quality.

Figure 8:
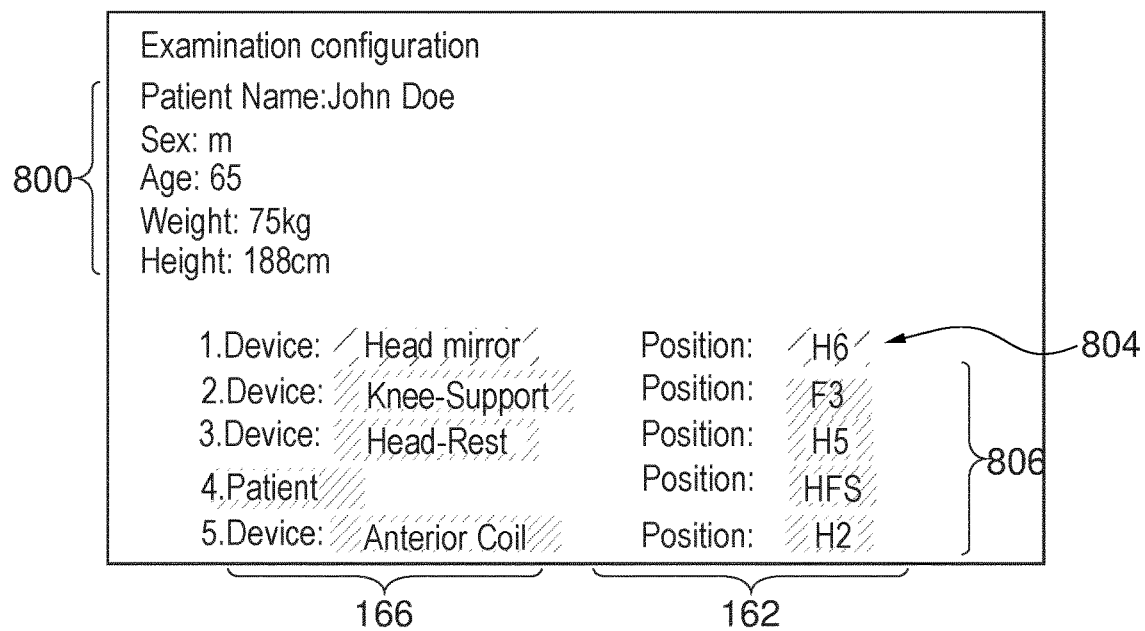
FIG. 8 illustrates and example of a user interface.
Figure 8:
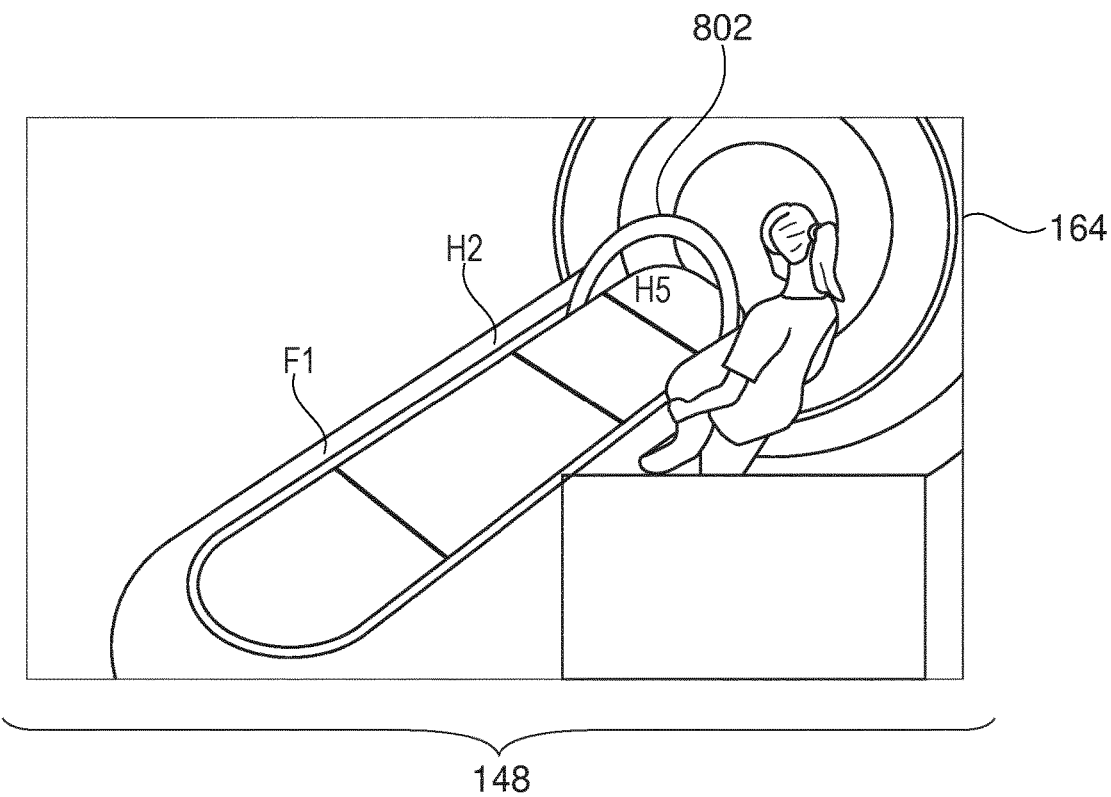

FIG. 8 illustrates an example of a user interface 148 that may be displayed. Camera data 164 is displayed along with subject information 800, the list of selected objects 160, and the selected coordinates 162. The list of placed objects, list of missing objects, and the list of misplaced objects may be used to modify or highlight the list of selected objects 160 and the selected coordinates 162. In this example, the head mirror 802 has already been correctly placed and may be marked using a highlight or different color on the display 148. As the figures are in black and white this is represented by labeling the head mirror with the label 804. The other items have not been placed and are labeled 806 display 148.

The user interface UI or display 148 is applicable to both initial and follow-up examination setups. The user is presented with a list to work along in order to configure the specific setup for the examination. The camera evaluates the items of the configuration, check-marks the completed items and highlights remaining to tasks to be completed. The algorithm specifically pays attention to correct and locked-in positions of the relevant setup components. The UI is presented to the user via a bore-side screen or directly onto the table via a projector. Both ways of displaying this guidance along with other means and combinations thereof are applicable.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 medical imaging system
102' magnetic resonance imaging system
104 imaging zone
106 radio therapy system
108 target zone
110 subject support
111 initial position 112 support surface
114 actuator
116 bore of imaging system
118 camera system
120 head rest
140 computer
142 processor
144 hardware interface
146 user interface
148 display (signal system)
150 memory
152 machine executable instructions
154 neural network
156 imaging protocol database
158 selection of a medical imaging protocol
160 list of selected objects
162 selected coordinates
164 camera data
166 list of placed objects
168 list of missing objects
170 list of misplaced objects
172 indicator
174 archive image
176 user interface control
200 operating position
202 subject
204 medical image data
206 medical image
300 medical instrument
304 magnet
309 region of interest
310 magnetic field gradient coils
312 magnetic field gradient coil power supply
314 radio-frequency coil
316 transceiver
320 pulse sequence commands
322 magnetic resonance imaging data
324 magnetic resonance image
400 receive a list of selected objects
402 signal the list of selected objects and the selected coordinate for each of the list of selected objects using the signal system
404 acquire the camera data using the camera system
406 input the camera data into the neural network to generate the list of placed objects
408 determine a list of missing objects by comparing the list of selected objects to the list of placed objects
410 indicate using the signal system the list of missing objects
412 determine a list of misplaced objects by comparing the selected coordinate for each of the list of objects to the coordinates of the placed objects on the support surface
414 indicate using the signal system the list of misplaced objects
500 medical imaging file
600 image
700 image
800 subject information
802 head mirror
804 correctly placed
806 not correctly placed

The invention claimed is:

1. A medical instrument comprising:
a subject support comprising a support surface configured to receive a subject;
a camera system configured to receive camera data descriptive of the support surface;
a signal system;
a memory configured to store machine executable instructions and a neural network, wherein the neural network is trained for generatingto generate a list of placed objects in response to inputting the camera data, wherein the list of placed objects identifies predetermined objects placed on the support surface and coordinates of the placed objects on the support surface;
a processor configured to control the medical instrument, wherein execution of the machine executable instructions further causes the processor to:
receive a list of selected objects, wherein the list of selected objects is selected from the predetermined objects, wherein the list of selected objects comprises a selected coordinate for each of the list of objects; and
signal the list of selected objects and the selected coordinate for each of the list of selected objects using the signal system;
wherein execution of the machine executable instructions further causes the processor to repeatedly:
acquire the camera data using the camera system;
input the camera data into the neural network to generate the list of placed objects;
determine a list of missing objects by comparing the list of selected objects to the list of placed objects;
indicate using the signal system the list of missing objects;
determine a list of misplaced objects by comparing the selected coordinate for each of the list of objects to the coordinates of the placed objects on the support surface; and
indicate using the signal system the list of misplaced objects.

2. The medical instrument of claim 1, wherein execution of the machine executable instructions further causes the processor to signal the list of selected objects in a sequential order defined in the list of selected objects using the signal system.

3. The medical instrument of claim 1, wherein execution of the machine executable instructions further causes the processor to determine a list of properly positioned objects using the list of placed objects, the list of missing objects, and the list of misplaced objects, wherein execution of the machine executable instructions further causes the processor to generate a signal if a member of the properly positioned objects is identified within the misplaced objects and/or the missing objects.

4. The medical instrument of claim 1, wherein the selected coordinate for each of the list of objects is specified in discrete coordinates, and wherein the coordinates of the placed objects on the support surface are specified in the discrete coordinates.

5. The medical instrument of claim 1, wherein the predetermined objects comprise the subject, wherein the neural network is further configured to identify a subject orientation.

6. The medical instrument of claim 1, wherein the predetermined objects comprise at least one selected from a group including: a cushion, a head mirror, a head rest, a knee rest, an arm rest, a magnetic resonance imaging coil, foot rest, or ankle rest.

7. The medical instrument of claim 1, wherein the medical instrument further comprises a medical imaging system configured to acquire medical image data from an imaging zone, wherein the support surface is configured to support at least a portion of the subject within the imaging zone.

8. The medical instrument of claim 7, wherein the medical imaging system is any one of the following, a magnetic resonance imaging system, a computed tomography system, a positron emission tomography system, or a single photon emission tomography system.

9. The medical instrument of claim 7, wherein the memory further comprises an imaging protocol database, wherein the imaging protocol database comprises lists of selected objects each associated with an imaging protocol, wherein execution of the machine executable instructions further causes the processor to:
receive a selection of a medical imaging protocol; and
retrieve the list of selected objects from the imaging protocol database using the selection of the medical imaging protocol.

10. The medical instrument of claim 1, wherein the subject support is configured to move from an initial position to an operating position, wherein in the initial position the camera system is configured to acquire the camera data descriptive of the support surface.

11. The medical instrument of claim 10, wherein execution of the machine executable instructions further causes the processor to:
repeatedly provide a user interface control using the signal system after repeatedly indicating using the signal system the list of missing objects and the list of misplaced objects;
generate an acceptance command if a signal is received from the user interface control;
move the subject support from the initial position to the operating position if the acceptance command is generated;
control the medical imaging system to acquire the medical image data when the subject support is in the operating position.

12. The medical instrument of claim 1, wherein the medical instrument further comprises a radiotherapy system configured for irradiating a target zone, wherein the support surface is configured to support at least a portion of the subject within the imaging zone.

13. The medical instrument of claim 1, wherein the camera system comprises at least one selected from a group including: a video camera, a camera, a color camera, a black and white camera, an infra-red camera, a thermal camera, multiple cameras, or a three-dimensional camera.

14. A non-transitory computer program product comprising: machine executable instructions for execution by a processor configured to control a medical instrument, wherein the medical instrument includes: a subject support comprising a support surface configured to receive a subject; a camera system configured to acquire camera data descriptive of the support surface; and a signal system;
wherein execution of the machine executable instructions further causes the processor to:
receive a list of selected objects; and
signal the list of selected objects and the selected coordinate for each of the list of selected objects using the signal system;
wherein execution of the machine executable instructions further causes the processor to repeatedly:
acquire the camera data using the camera system;
input the camera data into a neural network to generate a list of placed objects, wherein the neural network is trained to generate the list of placed objects in response to inputting the camera data, wherein the list of placed objects identifies predetermined objects placed on the support surface and coordinates of the placed objects on the support surface, wherein the list of selected objects is selected from the predetermined objects, wherein the list of selected objects comprises a selected coordinate for each of the list of objects;
determine a list of missing objects by comparing the list of selected objects to the list of placed objects;
indicate using the signal system the list of missing objects;
determine a list of misplaced objects by comparing the selected coordinate for each of the list of objects to the coordinates of the placed objects on the support surface; and
indicate using the signal system the list of misplaced objects, wherein execution of the machine executable instructions further causes the process to signal the list of selected objects in a sequential order defined in the list of selected objects using the signal system.

15. A method of operating a medical instrument, wherein the medical instrument comprises: a subject support comprising a support surface configured to receive a subject; a camera system configured to acquire camera data descriptive of the support surface; and a signal system;
wherein the method comprises:
receiving a list of selected objects; and
signaling the list of selected objects and the selected coordinate for each of the list of selected objects using the signal system;
wherein the method comprises repeatedly:
acquiring the camera data using the camera system;
inputting the camera data into a neural network to generate a list of placed objects, wherein the neural network is trained to generate the list of placed objects in response to inputting the camera data, wherein the list of placed objects identifies predetermined objects placed on the support surface and coordinates of the placed objects on the support surface, wherein the list of selected objects is selected from the predetermined objects, wherein the list of selected objects comprises a selected coordinate for each of the list of objects;
determining a list of missing objects by comparing the list of selected objects to the list of placed objects;
indicating using the signal system the list of missing objects;
determining a list of misplaced objects by comparing the selected coordinate for each of the list of objects to the coordinates of the placed objects on the support surface; and
indicating using the signal system the list of misplaced objects, wherein signaling the list of selected objects is performed in a sequential order defined in the list of selected objects using the signal system.

* * * * *